United States Patent [19]

Kato et al.

[11] 4,275,194

[45] Jun. 23, 1981

[54] CHITOSAN-IODINE ADDUCT

[75] Inventors: Masatada Kato, Tokyo; Nobuaki Mineshima, Mutsuzawamura; Tatsuo Kato, Mobara; Yoshiharu Kawada, Chiba; Hironori Hanada; Teiichi Inomata, both of Mobara, all of Japan

[73] Assignee: Nihon Tennen Gas Kogyo Co., Ltd., Tokyo, Japan

[21] Appl. No.: 936,047

[22] Filed: Aug. 23, 1978

[30] Foreign Application Priority Data

Nov. 26, 1977 [JP] Japan .................................. 52-141920
Dec. 28, 1977 [JP] Japan .................................. 52-157544

[51] Int. Cl.$^3$ ............................................ C08B 37/08
[52] U.S. Cl. ..................................... 536/20; 210/764; 424/76; 424/150; 424/180; 428/245; 536/122
[58] Field of Search .................................. 536/20, 122

[56] References Cited

U.S. PATENT DOCUMENTS

| 2,540,486 | 2/1951 | Minto ................................. 536/122 |
| 4,125,708 | 11/1978 | Masri et al. ......................... 536/20 |

OTHER PUBLICATIONS

Morak et al., "Nature", No. 4966, Jan. 2, 1965, p. 69.
Gaillard, "Nature", No. 5058, Oct. 8, 1966, pp. 202–203.
Gaillard et al., "Chemical Abstracts", vol. 66, 1967, p. 29018k.

*Primary Examiner*—Johnnie R. Brown
*Attorney, Agent, or Firm*—Armstrong, Nikaido, Marmelstein & Kubovcik

[57] ABSTRACT

A novel chitosan-iodine adduct wherein iodine is included in chitosan molecule is useful as a deodorant, a sterilizer or a disinfectant since the adduct holds iodine in a stable form and can release active iodine gradually into the environment as occasion demands. Also, a disinfectant fiber can be produced by sticking the chitosan-iodine adduct onto a fiber.

2 Claims, No Drawings

CHITOSAN-IODINE ADDUCT

FIELD OF THE INVENTION

The present invention relates to a novel chitosaniodine adduct. Further, the invention relates to the preparation and use of such a novel chitosan-iodine adduct.

SUMMARY OF THE INVENTION

As a result of the present inventors' studies, it has now been found that iodine combines very peculiarly with chitosan, which is a natural product, to form a substance different from both of these two starting substances. The formation of such a substance by an interaction between chitosan and iodine has heretofore not been known at all.

Chitosan has the following structure which is similar to the structure of starch.

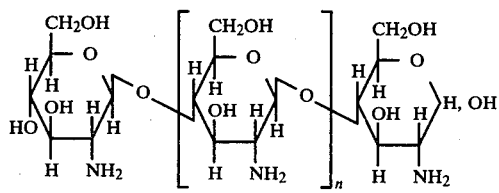

wherein n is a polymerization degree. Chitosan can be obtained by hydrolyzing chitin (acetylchitosan) constituting the frame of the Crustacea such as a lobster, a shrimp, a prawn, and a crab with, for example, caustic soda at an elevated temperature. It is said that its polymerization degree (n) depends upon the hydrolysis conditions but is usually about 2000 and thereby its molecular weight is from 200,000 to 400,000. The degree of deacetylation by hydrolysis depends also upon the reaction conditions, but the product becomes soluble in an acid solution if about 50% of chitin is deacetylated. Such a deacetylation product from chitin is known as a chitosan.

DESCRIPTION OF THE PREFERRED EMBODIMENTS

The present inventors have found that, when chitosan is brought into contact with iodine, chitosan combines with iodine firmly to give a product. It is seen from a comparison between chitosan, iodine, and this product with regard to their respective X-ray diffraction pattern that the product is not a mere mixture of chitosan and iodine. Chitosan and iodine each has a crystal face. (Their X-ray diffraction patterns have respectively a large peak.) On the other hand, the product is amorphous. (Its X-ray diffraction pattern is substantially linear and has no peak.) With regard to the combination mode of the chitosan-iodine adduct according to the present invention, it is considered that chitosan and iodine form an inclusion compound. Here, the term "inclusion compound" is used as a synonym for so-called "clathrate compound". For example, in a comparison of the IR absorption spectrum (KBr method) of the chitosan-iodine adduct with that of chitosan, these spectra coincide with each other and no change in the absorption portion of amino group (—NH$_2$) which is an active group in the chitosan molecule is observed. It is considered therefrom that iodine atoms are included in the lattice matrix provided by the chitosan molecule.

The formation of the chitosan-iodine adduct according to the present invention is carried out substantially instantaneously by, for example, contacting chitosan with a solution of iodine in any solvent (which may contain iodide ions). Chitosan is originally white in color but turns black on formation of said chitosan-iodine adduct. On the other hand, an iodine solution loses its blackish brown color. Therefore, the uptake of iodine by chitosan can be brought into a saturation state by supplementing iodine to contact it with chitosan until the iodine solution come to maintain its blackish brown color. It is quite surprising that chitosan reacts with iodine to form a chitosan-iodine adduct while natural chitin does not such an action. It is suitable to use water, a lower alcohol or a mixture thereof as a medium for contacting chitosan with an iodine solution. An iodide ion such as potassium iodide may be added to facilitate the dissolution of iodine. The contact of chitosan with an iodine solution may be carried out at any temperature, but about room temperature is convenient. The chitosan-iodine adduct formed can be separated as it is from the medium as a solid. The separated adduct does not readily lose its black color even if it is washed with water. It shows that iodine has been securely trapped in the molecular structrue of chitosan.

The thus formed chitosan-iodine adduct shows the general appearance of chitosan, that is, it is a substantially black flaky solid. When it is kept at a temperature of 80° C. or more, and particularly 100° C. or more, iodine rapidly vaporizes and the adduct is returned to white chitosan. Also, when it is further heated to a temperature of 200° C. or more, it is gradually carbonized without being molten. When the adduct is dipped in an aqueous alkali solution at room temperature, iodine is rapidly released and the adduct returns to white chitosan. Also, when the adduct is dipped in a dilute solution of a monobasic acid, the adduct is gradually dissolved to form a light brown solution. However, a precipitate is produced when the solution is allowed to stand for a long period of time. Also, when the adduct is dipped in neutral water, a very small amount of iodine is gradually liberated and the water turns light yellowish brown. The apparent specific gravity of the chitosan-iodine adduct is about 0.2. Also, even if the adduct is allowed to stand at room temperature in the form of a solid, it shows substantially no volatility. Thus, the irritating odor of iodine is not noticed and the adduct is substantially odorless.

According to one embodiment of the present invention, a very small amount of iodine can be collected by utilizing the chitosan-iodine adduct forming action as disclosed by the present invention. For example, as one of the processes for producing iodine from a natural brine containing a very small amount (e.g., about 100 ppm) of iodine, there is a process which comprises using an anion exchange resin. Here, the anion exchange resin can be replaced by chitosan. Chitosan is characterized in that it is superior to anion exchange resins in adsorption force, although the amount of iodine adsorbed is small, particularly in the case of a brine containing about 20 ppm of iodine. For example, a natural subterranean brine in Chiba Prefecture, Japan contains about 70 to about 120 ppm of iodine. An ion exchange resin, Amberlite K-400, is now commercially used for the recovery of iodine. The iodine recovery limit in this case does not exceed 80% by weight. On the other hand, the utilization of the chitosan-iodine adduct forming action according to the present invention is very advantageous in that iodine can further be recovered from said brine after the treatment with an ion exchange resin.

Also, the chitosan-iodine adduct according to the present invention can hold iodine in a stable form and can gradually release active iodine to the environment as occasion demands. Therefore, the adduct is useful in all fields utilizing such active iodine, for example, as a deodorant or a sterilizer. As one utilization method, the adduct may be used as a sterilizer or a disinfectant for drinking water, water for washing tableware or pool by packing the adduct in the form of flaky crystals having a suitable particle size into a container having pores and passing water therethrough at a suitable rate. Also, since chitosan which is a base for the chitosan-iodine adduct is sparingly soluble in neutral water, a very small amount of iodine can be liberated in bath water or wash water to sterilize or disinfect them by tieing up the chitosan-iodine adduct in a cloth and dipping the resulting package in a bathtub or a wash water tank for a flush toilet. The remainder after the completion of sterilization or disinfection in such a utilization of the adduct is chitosan which is a natural product. It is a large advantage from an ecological point of view. Thus, there is no fear of lacking safety as in synthesized chemicals as long as the chitosan-iodine adduct according to the present invention is employed.

As another use of the chitosan-iodine adduct according to the present invention, a disinfectant fiber can be prepared by sticking the adduct onto a fiber.

As the fiber used in this use, natural fibers, synthetic fibers and blended fibers of a natural fiber and a synthetic fiber may be enumerated. From the viewpoint of the adhesiveness of the chitosan-iodine adduct onto fibers, natural fibers are most preferable. As the natural fibers, cotton, silk, hemp, wool, etc. may be used. Blended fibers of a natural fiber and a synthetic fiber are almost equal to natural fibers in the adhesiveness to the chitosan-iodine adduct. On the other hand, synthetic fibers are poor in the adhesiveness to the chitosan-iodine adduct. Thus, the adduct is easily released by, for example, washing.

A process for producing a disinfectant fiber by sticking the chitosan-iodine adduct onto a fiber according to the present invention is as follows: Chitosan is first dissolved in an acid solution. A fiber is impregnated with the resulting acidic solution of chitosan and then dried to stick the chitosan fastly onto the fiber. Such a property of chitosan's being stuck onto a fiber is utilized for the reinforcement of paper, pulp, etc. The fiber containing the chitosan stuck thereonto is then dipped in an iodine-containing solution. Thus, iodine is reacted with the chitosan on the fiber to form a chitosan-iodine adduct in situ and thereby give a disinfectant fiber consisting of the fiber containing the chitosan-iodine adduct stuck thereonto.

The disinfectant fiber containing chitosan-iodine adduct stuck thereonto according to the present invention can be used as a bandage, a white overall, a padded adhesive plaster and an insole.

It is known that iodine shows sterilizing effect against many bacteria, and particularly colibacilli, in water at a concentration of about 1 ppm. For example, the following test data have been reported:

TABLE

Time Required to Achieve 99.99% Cell Destruction by Specified Free Halogen Residuals at pH 7.0 and 3° to 4° C.

| Microorganism | Chlorine 0.28 mg/l | Bromine 0.63 mg/l | Iodine 1.0 mg/l |
|---|---|---|---|
| Escherichia coli | $50^{sec.}$ | $60^{sec.}$ | $80^{sec.}$ |
| Aerobacter aerogenes | 40 | 75 | 60 |
| Pseudomonas aeruginosa | 45 | 70 | 110 |
| Salmonella senftenberg | 40 | 80 | 140 |
| Streptococcus faecalis | 170 | 210 | 340* |
| Staphylococcus aureus | 90 | 50 | 50 |

*Value obtained by extrapolation

Therefore, a satisfactory sterilizing effect can be provided to a fiber containing chitosan stuck thereonto by adding about 10 to about 100 ppm of iodine.

The following examples illustrate the present invention in more detail.

EXAMPLE 1

The chitosan used in this example as a starting material was prepared in the following manner:

The shell of Chinoecetes opilio and Paralithodes camtschaticus was dipped in a dilute (3 to 5% by weight) aqueous caustic soda solution overnight to dissolve off the protein, oils and fats, etc. contained in the shell. The thus treated shell was then dipped in dilute (about 3% by weight) hydrochloric acid to remove the calcium carbonate contained therein. The thus purified chitin was dipped in several times the weight of chitin of a concentrated (45% by weight or more) aqueous caustic soda solution, maintained at 80° to 100° C. for several hours, washed with water and then dried. When the product was dissolved in 3% acetic acid, the solution at a concentration of 0.5% by weight showed a viscosity of 200 to 800 centipoises at 20° C.

In 40 ml of an aqueous solution containing 4 g of iodine and 4 g of potassium iodide was dipped overnight 10 g of the thus obtained chitosan. The dipped chitosan was recovered by filtration and the mother liquor adhered thereonto was then removed by washing with water. The product was air-dried at a temperature of 30° C. or less to obtain 14.5 g of a chitosan-iodine adduct in the form of black flaky crystals. It was found by measuring the amount of the iodine remained in the filtration mother liquor and wash water after the collection of the chitosan-iodine adduct by filtration that the product contained about 3.4 g of iodine.

EXAMPLE 2

This example illustrates the recovery of iodine from a dilute iodine-containing brine with chitosan.

A column having a diameter of 12 cm and a height of 150 cm was packed with 100 g (about 1 l, apparent specific gravity 0.1) of chitosan. When 100 l of a brine containing 100 ppm of iodine, which had been added with the corresponding amount of chlorine, was passed through the packed column at a rate of 200 ml/min., about 9 g of iodine was adsorbed on chitosan and the iodine content of the brine passed was 8 to 12 ppm. Thus, about 109 g of a chitosan-iodine adduct was obtained.

Next, 150 ml of a 4% aqueous caustic soda solution was passed through the chitosan-iodine adduct. The iodine adsorbed was dissolved in the aqueous caustic soda solution according to the following reaction formula and the chitosan-iodine adduct was returned to original white chitosan.

$$6NaOH + 3I_2 \rightarrow 5NaI + NaIO_3 + 3H_2O$$

When sulfuric acid was added to the alkaline solution to acidify the solution, iodine was again liberated according to the following reaction formula:

$$5NaI + NaIO_3 + 3H_2O + 3H_2SO_4 \rightarrow 3I_2 + 6H_2O$$

The liberated iodine was collected by filtration. Thus, about 9 g of crude iodine was obtained. The white chitosan was repeatedly used as such in the next iodine adsorption.

EXAMPLE 3

In 600 ml of the brine containing 20 ppm of iodine obtained as a remainder when a natural subterranean brine containing about 100 ppm of iodine had been treated with Amberlite K-400 (an anion exchange resin) was dipped for 3 hours 1 g of the chitosan as obtained in Example 1. The dipped chitosan was subjected to the same subsequent treatments as in Example 1. Thus, 1 g of black flaky crystals of a chitosan-iodine adduct was obtained. It was found that the product contained about 10 mg of iodine.

As described above, iodine shows sterilizing effect against coli-bacilli in water at a concentration of about 1 ppm. The following examples show that said concentration of iodine as a sterilizer can be obtained by utilizing the chitosan-iodine adduct according to the present invention.

EXAMPLE 4

A column having a diameter of 12 cm and a height of 110 cm was packed with 200 g (apparent volume about 1 l) of a chitosan-iodine adduct containing about 30% by weight of iodine. Water was passed through the packed column at a rate of 10 l/min. The passed water contained 1 to 3 ppm of iodine.

EXAMPLE 5

In a cloth was tied up 10 g of a chitosan-iodine adduct containing about 30% by weight of iodine. The resulting package was dipped in 10 l of water, which was then gradually stirred. The concentration of iodine in water increased with the lapse of time and reached about 0.7 ppm after 5 minutes, 2.2 ppm after 15 minutes and 3 ppm after 20 to 25 minutes. Thus, the water had a satisfactory sterilizing action.

EXAMPLE 5

To 50 ml of 3% acetic acid was added 1 g of chitosan and the resulting mixture was stirred at room temperature to form a solution. Water was added to the solution to make the volume of the solution 1 l (a 0.1% by weight solution.) In the diluted solution was dipped about 100 g of bleached cotton cloth, which was pulled up immediately, squeezed well, and dried at 100° C. The cotton cloth contained about 0.1 to about 0.2% by weight of chitosan stuck thereonto. On the one hand, 0.02 g of iodine and 0.05 g of sodium iodide were dissolved in 10 ml of water. The resulting solution was diluted with water to about 500 ml. In the diluted solution was dipped 100 g of the above-mentioned cotton cloth containing about 0.1 to about 0.2% by weight of chitosan stuck thereonto. In about 10 minutes, almost all of the iodine contained in the solution was reacted with chitosan on the cotton cloth and the solution turned almost colorless. The cotton cloth turned light yellow. The cotton cloth was pulled up and dried at 40° C. by sending air thereto. Thus, a light yellow disinfectant fiber containing about 100 ppm of iodine was obtained.

What is claimed is:

1. A chitosan-iodine adduct wherein iodine is included in the molecule of chitosan.

2. A chitosan-iodine adduct wherein iodine is included in a molecule of chitosan, said adduct being the reaction product obtained by reacting solid phase chitosan with liquid phase iodine containing solution.

* * * * *